United States Patent
Ley et al.

(10) Patent No.: US 6,395,260 B1
(45) Date of Patent: May 28, 2002

(54) TOPICAL COSMETIC COMPOSITIONS COMPRISING BENZALDOXIMES

(75) Inventors: Jakob Peter Ley, Holzminden; William Johncock, Höxter, both of (DE)

(73) Assignee: Haarmann & Reimer GmbH, Holzminden (DE)

( * ) Notice: Subject to any disclaimer, the term of this patent is extended or adjusted under 35 U.S.C. 154(b) by 0 days.

(21) Appl. No.: 09/609,010

(22) Filed: Jun. 30, 2000

(30) Foreign Application Priority Data

Jul. 8, 1999 (DE) .......................................... 199 31 707
Jan. 26, 2000 (DE) .......................................... 100 03 234

(51) Int. Cl.[7] .............................. A61K 7/42; A61K 7/44; A61K 7/06
(52) U.S. Cl. .......................... 424/59; 424/60; 424/70.1; 424/401; 514/507
(58) Field of Search ..................... 424/401, 59, 70.1, 424/60; 514/507

(56) References Cited

FOREIGN PATENT DOCUMENTS

EP 672746 A1 * 9/1995
WO 95/01157 1/1995

OTHER PUBLICATIONS

Cosmetic & Toiletries, May 1996, vol. 111, pp. 43–51, Giuseppe Prota, PhD, Melanins and Melanogenesis.
Chem. Ber. (month unavailable) 1883, 16, pp. 1780–1787, B. Lach: Zur Kenntniss der Aldoxime.
Chem. Ber. (month available) 1941, 74, pp. 79–89, Faltis et al. Über Biscoclaurin–Alkaloide: Die Konstitution des Chondodendrine und des Trilobins.
Chem. Ber. (month unavailable) 1922, 55, pp. 920–929, Ott et al, Über die Vanillin–Isomeren Der Resorcyl–Reihe.
Chem. Ber. (month unavailable) 1922, 55, pp. 2357–2372, Rosenmund et al, Zur Kenntnis des Gallusaldehyds und seiner Derivate.
Liebigs Ann. (month unavailable) 1936, 526, pp. 277–294, Neber et al, Eine neue, allgemeine Methode zur Gewinnung von $\alpha,\gamma$—Diamino—ketoverbindungen. III.

* cited by examiner

Primary Examiner—Jose' G. Dees
Assistant Examiner—Marina Lamm
(74) Attorney, Agent, or Firm—Joseph C. Gil; Noland J. Cheung

(57) ABSTRACT

Benzaldoximes having at least one aromatic hydroxyl or alkoxy group are effective constituents in topical cosmetic compositions, in particular, skin lightening compositions.

7 Claims, No Drawings

TOPICAL COSMETIC COMPOSITIONS COMPRISING BENZALDOXIMES

FIELD OF THE INVENTION

The invention relates to topical cosmetic compositions, in particular, skin lightening compositions, comprising benzaldoximes having at least one aromatic hydroxyl or alkoxy group for cosmetic or dermatological applications.

BACKGROUND OF THE INVENTION

Skin-lightening active ingredients somehow interfere with melanin metabolism or catabolism. The melanins, which are usually brown to black in color, are formed in the melanocytes of the skin, transferred to the keratinocytes and cause the coloration of skin or hair. The brown-black eumelanins are formed in mammals predominantly from hydroxy-substituted aromatic amino acids such as L-tyrosine and L-DOPA, and the yellow to red pheomelanins are additionally formed from sulfur-containing molecules (Cosmetics & Toiletries 1996, 111 (5), 43–51). Starting from L-tyrosines, the copper-containing key enzyme tyrosinase forms L-3,4-dihydroxyphenylalanine (L-DOPA), which for its part is oxidized again by the tyrosinase via the red-brown dopaquinone to give melanin. A comparison of tyrosinases from plants, fungi and mammals shows that the mechanism and the substrate specificity is comparable in all of the tyrosinases examined.

If, for some reason, the melanin-forming melanocytes are not distributed evenly in the human skin, pigmentation spots form, which are either lighter or darker than the surrounding areas of skin. In order to overcome this problem, skin lightening compositions are offered on the market which help to at least partially even out pigmentation spots. In addition, many people have a desire to lighten their naturally dark skin color. Very safe and effective skin lightening compositions are required for this purpose. Many skin lightening compositions comprise tyrosinase inhibitors of greater or lesser strength.

Commercially available skin lightening compositions comprise, in particular, hydroquinone, hydroquinone derivatives, such as, for example, arbutin, vitamin C, derivatives of ascorbic acid, such as, for example, ascorbyl palmitate, kojic acid and derivatives of kojic acid, such as, for example, kojic acid dipalmitate.

One of the most frequently used skin lighteners is hydroquinone. However, the substance has a cytotoxic effect towards melanocytes and can damage the skin. For this reason, such preparations are no longer authorized for cosmetic applications in, for example, Japan and South Africa. In addition, hydroquinone is very oxidation-sensitive and can only be stabilized, with difficulty, in cosmetic formulations.

Vitamin C and ascorbic acid derivatives have only an inadequate action on the skin. Further, they do not act directly as tyrosinase inhibitors, but reduce the colored intermediates of melanin biosynthesis.

Kojic acid (5-hydroxy-2-hydroxymethyl-4-pyranone) is a tyrosinase inhibitor which, by chelating the copper atoms of the enzyme, inhibits the catalytic activity of the latter; it is used in commercial skin lightening compositions. The substance is formed predominantly in Aspergillus cultures and can only be isolated therefrom in small amounts.

SUMMARY OF THE INVENTION

The object of the present invention was to find low-cost, easy-to-prepare, highly effective tyrosinase inhibitors which can be used as active ingredients in skin lightening compositions.

The invention relates to topical cosmetic compositions comprising benzaldoximes of the general formula

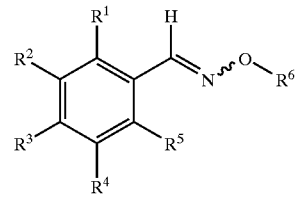

geometric isomers thereof or mixtures of these isomers
wherein
$R^1$, $R^5$ independently of one another are hydrogen atoms or alkyl groups having from 1 to 4 carbon atoms,
$R^2$, $R^3$ and $R^4$ independently of one another are hydrogen atoms, hydroxyl groups, alkyl groups having from 1 to 4 carbon atoms or —O—$R^7$ groups, where $R^7$ can be an alkyl group having from 1 to 4 carbon atoms or an arylalkyl group having from 7 to 10 carbon atoms,
with the proviso that at least one of the radicals $R^2$ to $R^4$ is a hydroxyl group or an —O—$R^7$ group, where $R^7$ is as defined above,
and
$R^6$ is a hydrogen atom, an alkyl or alkenyl group having from 1 to 12 carbon atoms or an optionally substituted aryl or arylalkyl group having from 7 to 10 carbon atoms or an optionally substituted heteroaryl or heteroarylalkyl group having from 2 to 10 carbon atoms which contain one or more heteroatoms from the group consisting of sulfur, nitrogen and oxygen.

DETAILED DESCRIPTION OF THE INVENTION

Preference is given to topical cosmetic compositions comprising benzaldoximes of the general formula

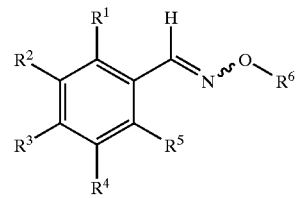

geometric isomers thereof or mixtures of these isomers,
wherein
$R^1$ and $R^5$ are hydrogen,
and
$R^2$, $R^3$ and $R^4$ independently of one another are hydrogen atoms, hydroxyl groups, alkyl groups having from 1 to 4 carbon atoms or —O—$R^7$ groups, where $R^7$ can be an alkyl group having from 1 to 4 carbon atoms or an arylalkyl group having from 7 to 10 carbon atoms,
with the proviso that at least one of the radicals $R^2$ to $R^4$ is a hydroxyl group or an —O—$R^7$ group, where $R^7$ is as defined above,
and
$R^6$ is a hydrogen atom, an alkyl or alkenyl group having from 1 to 12 carbon atoms or an optionally substituted arylalkyl group having from 7 to 10 carbon atoms.

Particular preference is given to topical cosmetic compositions comprising benzaldoximes chosen from the group comprising, for example, 4-hydroxybenzaldoxime;
3,4,5-trihydroxybenzaldoxime;
3-hydroxy-4-methoxybenzaldehyde O-ethyloxime;
3-ethoxy-4-hydroxybenzaldehyde O-ethyloxime;
3,4-dihydroxybenzaldoxime;
3-hydroxy-4-methoxybenzaldoxime;
4-hydroxy-3-methoxybenzaldehyde O-ethyloxime;
3,4-dihydroxybenzaldehyde O-(4-methylbenzyl)-oxime;
3-ethoxy-4-hydroxybenzaldoxime;
4-hydroxy-3-methoxybenzaldoxime;
3,4-dihydroxybenzaldehyde O-ethyloxime;
but not limited thereto.

Surprisingly, we have now found that the benzaldoximes present in the topical compositions according to the present invention are particularly effective tyrosinase inhibitors. In particular, many of the benzaldoximes according to the present invention are significantly more effective than kojic acid. They can, therefore, be used as active ingredients in cosmetic or dermatological skin lightening compositions.

The topical cosmetic compositions according to the present invention, in particular, skin lightening compositions comprising the benzaldoximes are prepared by customary methods known per se by incorporating one or more of the benzaldoximes according to the present invention into cosmetic or dermatological formulations which have the customary composition and, in addition to the skin lightening action, can also be used for the treatment, care and cleansing of skin or hair and as make-up products in decorative cosmetics.

Accordingly, the present invention also relates to topical cosmetic compositions, in particular, cosmetic and dermatological skin lightening compositions, which comprise the benzaldoximes, according to the present invention, in an effective amount alongside other, otherwise customary composition constituents. They comprise from 0.01% by weight to 30% by weight, preferably from 0.01 to 20% by weight, but, in particular, from 0.01% by weight to 5% by weight, based on the total weight of the formulation, of the benzaldoximes according to the present invention and can be in the form of "water-in-oil", "oil-in-water", "water-in-oil-in-water" or "oil-in-water-in-oil" emulsions, microemulsions, gels, solutions, e.g., in oils, alcohols or silicone oils, sticks, soaps, aerosols, sprays and also foams. Further customary cosmetic auxiliaries and additives can be present in amounts from 5 to 99% by weight, preferably from 10 to 80% by weight, based on the total weight of the formulation. In addition, the formulations can comprise water in an amount up to 99.99% by weight, preferably from 5 to 80% by weight, based on the total weight of the formulation.

Some of the benzaldoximes present in the skin lightening compositions according to the present invention are known. The known benzaldoximes according to the present invention are described, for example, in Chem. Ber. 1883, 16, 1780 to 1787, Chem. Ber. 1941, 74, 79, 87 and 89, Chem. Ber. 1922, 55, 920 to 929, in Chem. Ber. 1922, 55, 2357 to 2372 and in Liebigs Ann. 1936, 526, 277 to 294. References to an action as tyrosinase inhibitors and their use in cosmetic and/or dermatological preparations are not made. The benzaldoximes according to the present invention present in the skin lightening compositions are, if still unknown, prepared by processes known to the person skilled in the art by reacting the corresponding benzaldehydes with the corresponding hydroxylamines or salts thereof in a solvent, preferably in water, an aliphatic alcohol having from 1 to 4 carbon atoms or a mixture of these solvents, using an auxiliary base, preferably sodium hydroxide or sodium acetate, at 0° C. to 120° C., preferably 20° C. to 100° C., where appropriate, neutralized with a mineral acid and purified using the customary methods, preferably by crystallization.

The benzaldehydes used are preferably 4-hydroxybenzaldehyde, 3,4,5-trihydroxybenzaldehyde (gallaldehyde), 4-methoxy-3-hydroxy-benzaldehyde (isovanillin), 3-ethoxy-4-hydroxybenzaldehyde (ethylvanillin), 3,4-dihydroxybenzaldehyde (protocatechualdehyde) or 4-hydroxy-3-methoxybenzaldehyde (vanillin).

Preferred hydroxylamines are hydroxylamine, O-ethylhydroxyl-amine or O-4-methylbenzylhydroxylamine or the salts of the said hydroxylamines.

The topical cosmetic compositions according to the present invention, in particular, skin lightening compositions, can comprise cosmetic auxiliaries and additives, as are usually used in such preparations, e.g., sunscreens (e.g., organic or inorganic light filter substances, preferably micropigments), preservatives, bactericides, fungicides, virucides, ingredients which have a cooling action, plant extracts, antiinflammatory active ingredients, substances which accelerate wound healing (e.g., chitin or chitosan and derivatives thereof), film-forming substances (e.g., polyvinylpyrrolidones or chitosan or derivatives thereof), customary antioxidants, vitamins (e.g., vitamin C and derivatives, tocopherols and derivatives, vitamin A and derivatives), 2-hydroxycarboxylic acids (e.g., citric acid, malic acid, L-, D- or dl-lactic acid), skin lighteners (e.g., kojic acid, hydroquinone or arbutine), skin colorants (e.g., walnut extracts or dihydroxyacetone), perfumes, antifoams, dyes, pigments which have a coloring action, thickeners, surface-active substances, emulsifiers, emollients, humectants and/or moisturizers (e.g., glycerol or urea), fats, oils, unsaturated fatty acids or derivatives thereof (e.g., linoleic acid, ($\alpha$-linolenic acid, $\gamma$-linolenic acid or arachidic acid and the natural or synthetic esters thereof in each case), waxes or other customary constituents of a cosmetic or dermatological formulation, such as alcohols, polyols, polymers, foam stabilizers, electrolytes, organic solvents, silicone derivatives or chelating agents (e.g., ethylenediaminetetraacetic acid and derivatives).

The amounts of cosmetic or dermatological auxiliaries and additives and perfume to be used in each case can easily be determined by simple exploratory experiments by the person skilled in the art, depending on the nature of the product in question.

Preferably, the skin lightening compositions according to the present invention comprising the benzaldoximes according to the present invention can also comprise other active ingredients for skin lightening. In particular, the skin lightening compositions according to the present invention can also comprise kojic acid, kojic acid derivatives, ascorbic acid, ascorbic acid derivatives, hydroquinone, hydroquinone derivatives, sulfur-containing molecules, such as, for example, glutathione or cysteine or other synthetic or natural active ingredients for skin lightening, it being possible for the latter to be used also in the form of an extract from plants, such as, for example, bearberry extract and rice extract.

The amount of the abovementioned exemplary other active ingredients for skin lightening (one or more compounds), which are not identical to the benzaldoximes present in the skin lightening compositions according to the present invention, can be, in the skin lightening compositions according to the present invention, from 0.01 to 30% by weight, preferably from 0.01 to 20% by weight, particularly preferably from 0.01 to 5% by weight, based on the total weight of the preparation.

The skin lightening compositions according to the present invention comprising the benzaldoximes according to the present invention can, however, also additionally comprise UVA and/or UVB filter substances, where the total amount of filter substances may be from 0.1 to 30% by weight, preferably from 0.5 to 10% by weight, based on the total weight of the preparations, giving, for example, sunscreens for skin and hair. Examples of UV filter substances which can be used are 3-benzylidenecamphor derivatives (e.g., 3-(4-methylbenzylidene)-dl-camphor), amino-benzoic acid derivatives (e.g., 2-ethylhexyl 4-(N,N-dimethylamino) benzoate or methyl anthranilate), 4-methoxycinnamates (e.g., 2-ethylhexyl p-methoxycinnamate or isoamyl p-methoxycinnamate), benzophenones (e.g., 2-hydroxy-4-methoxybenzophenone), mono- or polysulphonated UV filters [e.g., 2-phenylbenzimidazole-5-sulphonic acid, sulisobenzones or 1,4-bis(benzimidazolyl)-benzene-4,4',6,6'-tetrasulphonic acid and 3,3'-(1,4-phenylenedimethylidene)-bis-(7,7-dimethyl-2-oxo-bicyclo-[2,2,1]heptane-1-methanesulphonic acid) and salts thereof), salicylates (e.g., 2-ethylhexyl salicylate or homomethyl salicylate), triazines (e.g., 2,4-bis-[4-(2-ethylhexyloxy)-2-hydroxyphenyl]-6-(4-methoxyphenyl)-1,3,5-triazine, bis-(2-ethylhexyl) 4,4'-([6-([(1,1-dimethylethyl)-aminocarbonyl]phenylamino)-1,3,5-triazin-2,4-diyl] dimino)bisbenzoate), 2-cyanopropenoic acid derivatives (e.g., 2-ethylhexyl 2-cyano-3,3-diphenyl-2-propenoate), dibenzoyl derivatives (e.g., 4-tert.-butyl-4'-methoxydibenzoylmethane), polymer-bonded UV filters (e.g., polymer of N-[2-(or 4)-(2-oxo-3-bomylidene)methyl]-benzylacrylamide) or pigments (e.g., titanium dioxides, zirconium dioxides, iron oxides, silicon dioxides, manganese oxides, aluminium oxides, cerium oxides or zinc oxides).

The lipid phase in the topical cosmetic compositions according to the present invention can advantageously be chosen from the following groups of substances: mineral oils (advantageously paraffin oil), mineral waxes, hydrocarbons (advantageously squalane or squalene), synthetic or semisynthetic triglyceride oils (e.g., triglycerides of capric or caprylic acid), natural oils (e.g., castor oil, olive oil, sunflower oil, soya oil, peanut oil, rapeseed oil, almond oil, palm oil, coconut oil, palm kernel oil, borage oil seed oil and the like), natural ester oils (e.g., jojoba oil), synthetic ester oils (preferably esters of saturated and/or unsaturated, linear and/or branched alkanecarboxylic acids carrying from 3 to 30 carbon atoms with saturated and/or unsaturated, linear and/or branched alcohols having from 3 to 30 carbon atoms and esters of aromatic carboxylic acids with saturated and/or unsaturated, linear and/or branched alcohols having from 3 to 30 carbon atoms, in particular, chosen from the group consisting of isopropyl myristate, isopropyl stearate, isopropyl palmitate, isopropyl oleate, n-butyl stearate, n-hexyl laurate, n-decyl laurate, isooctyl stearate, isononyl stearate, isononyl isononanoate, 2-ethylhexyl palmitate, 2-ethylhexyl laurate, 2-hexyldecyl stearate, 2-octyldecyl palmitate, oleyl oleate, oleyl erucate, erucyl oleate, erucyl erucate, and synthetic or natural mixtures of such esters), fats, waxes and other natural and synthetic fatty substances, preferably esters of fatty alcohols with alcohols of low carbon number (e.g., with isopropanol, propylene glycol or glycerol) or esters of fatty alcohols with alkanoic acids of low carbon number or with fatty acids, alkyl benzoates (e.g., mixtures of n-dodecyl, n-tridecyl, n-tetradecyl and n-pentadecyl benzoate), and cyclic or linear silicone oils (such as, for example, dimethylpolysiloxanes, diethylpolysiloxanes, diphenylpolysiloxanes, and mixed forms thereof).

The aqueous phase of the topical cosmetic compositions according to the present invention optionally, advantageously comprises alcohols, diols or polyols of low carbon number, and ethers thereof, preferably ethanol, isopropanol, propylene glycol, glycerol, ethylene glycol, ethylene glycol monoethyl or monobutyl ethers, propylene glycol monomethyl, monoethyl or monobutyl ethers, diethylene glycol monomethyl or monoethyl ethers and analogous products, and also alcohols of low carbon number, e.g., ethanol, isopropanol, 1,2-propanediol, glycerol, and also α- or β-hydroxy acids, preferably lactic acid, citric acid or salicylic acid, and also emulsifiers, which may be advantageously chosen from the group consisting of ionic, nonionic, polymeric, phosphate-containing and zwitterionic emulsifiers, and, in particular one or more thickeners, which may advantageously be chosen from the group consisting of silicon dioxide, aluminium silicates, such as, for example, bentonites, polysaccharides and derivatives thereof, e.g., hyaluronic acid, guar flour, xanthan gum, hydroxypropylmethylcellulose or allulose derivatives, particularly advantageously from the group of polyacrylates, preferably, a polyacrylate from the group of so-called Carbopols, in each case individually or in combination, or from the group of polyurethanes.

For use, the topical cosmetic compositions according to the present invention, in particular, the skin lightening compositions, comprising the benzaldoximes according to the present invention are applied to the skin and/or hair in a sufficient amount in a manner customary for cosmetics.

The invention is further illustrated but is not intended to be limited by the following examples in which all parts and percentages are by weight unless otherwise specified.

EXAMPLES

Example 1

"Oil-in-water" Emulsion

| Part | Raw material name (manufacturer) | Chemical name | Content in % by weight |
|---|---|---|---|
| A | Arlatone 983 S ® (ICI) | ether of polyethylene glycol with glyceryl monostearate | 1.2 |
|   | Brij 76 ® (ICI) | 3, 6, 9, 12, 15, 18, 21, 24, 27, 30, 33, 36-decaoxaoctatetracontan-1-ol | 1.2 |
|   | Cutina MD ® (Henkel) | glyceryl monostearate | 3.5 |
|   | Baysilone oil M10 ® (GE Bayer) | polydimethylsiloxane | 0.8 |
|   | Eutanol G ® (Henkel) | octyldodecanol | 3.0 |
|   | Paraffin oil 65 cp (Henry Lamotte) | mineral oil | 8.0 |
| B | Water, dist. |  | 49.6 |
|   | Phenopip ® (Nipa Laboratories) | 2-phenoxyethanol and methyl 4-hydroxy-benzoate and ethyl 4-hydroxybenzoate and propyl 4-hydroxy-benzoate and butyl 4-hydroxybenzoate | 0.5 |
|   | Trilon BD ® (BASF) | disodium EDTA | 0.1 |
|   | 1,2-Propylene glycol |  | 2.0 |
|   | Glycerol 99% |  | 3.0 |
|   | 4-Hydroxy-3-methoxy-benzaldoxime |  | 0.2 |
| C | Water, dist. |  | 25.0 |
|   | Carbopol 2050 ® (B. F. Goodrich) | crosslinked acrylic acid/ $C_{10}$–$C_{30}$-alkyl acrylate polymer | 0.4 |
|   | Aqueous sodium hydroxide solution, 10% |  | 1.2 |
| D | Perfume oil |  | 0.3 |

Part A was mixed and heated to 80° C. Part B was mixed and heated to 90° C. and added to part A with stirring. For part C, Carbopol was carefully dispersed in water and neutralized with sodium hydroxide solution (pH 6.9). Part C was then added at 60° C. to the mixture of parts A and B. Part D was added to the mixture of parts A, B and C at room temperature.

Example 2

"Water-in-oil" Emulsion with UVA/B Broad-band Protection

| Part | Raw material name (manufacturer) | Chemical name | Content in % by weight |
|---|---|---|---|
| A | Dehymuls PGPH ® (Henkel) | polyglycerol-2 dipolyhydroxystearate | 3.0 |
|   | Monomuls 90-O 18 ® (Henkel) | glyceryl oleate | 1.0 |
|   | Permulgin 2550 ® (Koster Keunen Holland) | beeswax | 1.0 |
|   | Myritol 318 ® (Henkel) | caprylic/capric triglycerides | 6.0 |
|   | Witconol TN ® (Witco) | $C_{12}$–$C_{15}$-alkyl benzoate | 6.0 |
|   | Cetiol SN ® (Henkel) | cetyl and stearyl isononanoate | 5.0 |
|   | Copherol 1250 ® (Henkel) | tocopherol acetate | 1.0 |
|   | Solbrol P ® (Bayer) | propyl 4-hydroxybenzoate | 0.1 |
|   | Neo Heliopan ® AV (Haarmann & Reimer) | 2-ethylhexyl p-methoxycinnamate | 4.0 |
|   | Neo Heliopan ® E 1000 (Haarmann & Reimer) | isoamyl p-methoxycinnamate | 4.0 |
|   | Neo Heliopan ® MBC (Haarmann & Reimer) | 3-(4-methylbenzylidene)-dl-camphor | 2.0 |
|   | Neo Heliopan ® OS (Haarmann & Reimer) | 2-ethylhexyl salicylate | 3.0 |
|   | Octyltriazone |  | 1.0 |
|   | Zinc oxide neutral (Haarmann & Reimer) |  | 7.0 |
| B | Water, dist. |  | 39.8 |
|   | Trilon BD ® (BASF) | disodium EDTA | 0.1 |
|   | Phenoxyethanol |  | 0.7 |
|   | Solbrol M (Bayer) | methyl 4-hydroxybenzoate | 0.2 |
|   | Glycerol 99% |  | 4.0 |
|   | Neo Heliopan ® Hydro (Haarmann & Reimer), 15% as sodium salt | 2-phenylbenzimidazole-5-sulphonic acid | 10.0 |
|   | Benzophenone-4 |  | 0.5 |
|   | 4-Hydroxy-3-methoxybenzaldoxime |  | 0.2 |
| C | Perfume oil |  | 0.3 |
|   | Bisabol |  | 0.1 |

For part A, all of the substances except zinc oxide were heated to 85° C., and the zinc oxide was carefully dispersed in the mixture. The components of part B were mixed, heated to 85° C. and added to part A with stirring. Part C was added to the mixture of parts A and B and then the mixture was homogenized using a dispersing tool.

Example 3

"Oil-in-water" Emulsion with UVA/B Broad-band Protection

| Part | Raw material name (manufacturer) | Chemical name | Content in % by weight |
|---|---|---|---|
| A | Arlacel 165 ® (ICI) | glyceryl stearate and polyethylene glycol 100 stearate | 3.0 |
|   | Emulgin B2 ® (Henkel) | ceteareth-20 | 1.0 |
|   | Lanette O ® (Henkel) | cetyl and stearyl alcohol | 1.15 |
|   | Myritol 318 ® (Henkel) | caprylic/capric triglycerides | 5.0 |
|   | Cetiol SN ® (Henkel) | cetyl and stearyl isononanoate | 4.0 |
|   | Abil 100 ® (Goldschmidt) | polydimethylsiloxane | 1.0 |
|   | Bentone Gel MIO ® (Rheox) | mineral oil and quaternium-18 hectorite and propylene carbonate | 3.0 |
|   | Cutina CBS ® (Henkel) | glyceryl stearate and cetyl alcohol and stearyl alcohol and cetyl palmitate and cocoglycerides | 2.0 |
|   | Neo Heliopan ® 303 (Haarmann & Reimer) | 2-ethylhexyl-2-cyano-3,3-diphenyl-2-propenoate | 7.0 |
|   | Neo Heliopan ® BB (Haarmann & Reimer) | 2-hydroxy-4-methoxybenzophenone | 1.0 |
|   | Neo Heliopan ® MA (Haarmann & Reimer) | menthyl anthranilate | 3.0 |
|   | 2-Ethylhexyl N,N-di-methyl-4-aminobenzoate |  | 3.0 |
|   | Titanium dioxide microfine |  | 5.0 |
| B | Water, dist. |  | 55.65 |
|   | Trilon BD ® (BASF) | disodium EDTA | 0.1 |
|   | Veegum ultra ® (Vanderbilt) | magnesium aluminium sulphate | 1.0 |
|   | Natrosol 250 HHR (Aqualon) | hydroxymethylcellulose | 0.3 |
|   | Glycerol |  | 3.0 |
|   | Phenopip ® (Nipa Laboratories) | 2-phenoxyethanol and methyl 4-hydroxybenzoate and ethyl 4-hydroxybenzoate and propyl 4-hydroxybenzoate and butyl 4-hydroxybenzoate | 0.3 |
|   | 4-Hydroxy-3-methoxybenzaldoxime |  | 0.2 |
| C | Perfume oil |  | 0.3 |

For part A, all of the substances apart from titanium dioxide were mixed and heated to 85° C.; the titanium dioxide was carefully dispersed into the mixture. For part B, all of the substances apart from Veegum and Natrosol were mixed and heated to 90° C., Natrosol and Veegum were dispersed into the mixture, which was added to part A with stirring. Part C was added to the mixture of parts A and B and then the mixture was homogenized using a dispersing tool.

Example 4

"Oil-in-water" Emulsion with UVA/B Broad-band Protection

| Part | Raw material name (manufacturer) | Chemical name | Content in % by weight |
|---|---|---|---|
| A | Crodaphos MCA ® (Croda) | cetyl phosphate | 1.50 |
|   | Cutina MD ® (Henkel) | glyceryl stearate | 2.0 |
|   | Lanette 16 ® (Henkel) | cetyl alcohol | 1.2 |
|   | Myritol 318 ® (Henkel) | caprylic/capric triglycerides | 5.0 |

| Part | Raw material name (manufacturer) | Chemical name | Content in % by weight |
|---|---|---|---|
| | Cetiol SN ® (Henkel) | cetyl and stearyl isononanoate | 5.0 |
| | Copherol 1250 ® (Henkel) | tocopherol acetate | 0.5 |
| | Solbrol P ® (Bayer) | propyl 4-hydroxy-benzoate | 0.1 |
| | Abil 100 ® (Goldschmidt) | polydimethylsiloxane | 0.3 |
| | Trilon BD ® (BASF) | disodium EDTA | 0.1 |
| | Neo Heliopan ® HMS (Haarmann & Reimer) | 3,3,5-trimethylcyclohexyl salicylate | 5.0 |
| | Butylmethoxydibenzoyl-methane | | 2.0 |
| B | Water, dist. | | 47.6 |
| | 1,3-Butylene glycol | | 3.0 |
| | Sobrol M ® (Bayer) | methyl 4-hydroxy-benzoate | 0.2 |
| | Phenoxyethanol | | 0.7 |
| | Carbopol 2050 ® (B. F. Goodrich) | acrylic acid/$C_{10}$–$C_{30}$-alkyl acrylate polymer | 0.2 |
| | Keltrol T ® (Calgon) | xanthan gum | 0.2 |
| | Neo Heliopan ® AP (Haarmann & Reimer) | 2,2-(1,4-phenylene-bis-(1H-benzimidazole-4,6-disulphonic acid) and disodium salt | 22 |
| | 4-Hydroxy-3-methoxy-benzaldoxime | | 0.2 |
| C | Aqueous sodium hydroxide solution, 10% | | 2.8 |
| D | Perfume oil | | 0.3 |
| | Bisabolol | | 0.1 |

Part A was heated to 85° C. Carbopol and Keltrol were dispersed into the remaining constituents while cold, the mixture was heated to 85° C. and added to part A. Part C was immediately added to the mixture of parts A and B at 80° C. and homogenized for minutes using a dispersing tool. Part D was finally added at room temperature and the mixture was homogenized using a dispersing tool.

Synthesis Procedure for the Benzaldoximes

The benzaldehyde (87 mmol) was dissolved in 45 ml of water at 40° C. A solution of the corresponding hydroxylamine hydrochloride (90 mmol) and of sodium acetate (87 mmol) in 25 ml of water was added, and the reaction mixture was stirred at about 80° C. for 2 h under nitrogen. The mixture was cooled and extracted with 200 ml of tert-butyl methyl ether, the organic phase was washed with saturated sodium chloride solution, dried over sodium sulphate and filtered, and the filtrate was evaporated to dryness tinder reduced pressure. If necessary, the crystalline residue was recrystallized.

TABLE 1

| Test compound | Name | CAS No. | m.p./° C. | MS |
|---|---|---|---|---|
| 1 | 4-hydroxybenzaldoxime | 699-06-9 | 86.3 | EI: m/e = 137 (100%), 120 (14%), 119 (16%), 94 (71%), 93 (21%), 65 (39%), 64 (12%), 63 (15%), 53 (10%), 39 (21%) |
| 2 | 3,4,5-trihydroxybenzaldoxime | 53148-14-4 | 177 (decomp) | APCI-(+): m/e = 170.0 (100%), 154. (11%) |
| 3 | 3-hydroxy-4-methoxy-benzaldehyde O-ethyloxime | — | 61.4 | EI: m/e = 195 (199%), 140 (20%), 124 (36%), 123 (27%), 106 (21%), 79 (22%), 65 (22%), 52 (25%), 51 (22%), 29 (27%) |
| 4 | 3-ethoxy-4-hydroxy-benzaldehyde O-ethyloxime | — | 43 | EI: m/e = 209 (100%), 153 (39%), 152 (25%), 136 (26%), 126 (28%), 110 (36%), 52 (23%), 51 (20%), 29 (40%), 27 (26%) |
| 5 | 3,4-dihydroxybenzaldoxime | 3343-59-7 | 143 (decomp) | ESI-(−): m/e = 305.0 (100%), 152.2 (80%) |
| 6 | 3-hydroxy-4-methoxy-benzaldehyde | 51673-94-0 | 142.4 | EI: m/e = 167 (100%), 152 (31%), 134 (14%), 125 (14%), 124 (52%), 109 (15%), 106 (16%), 79 (20%), 52 (19%), 51 (21%) |
| 7 | 4-hydroxy-3-methoxy-benzaldehyde O-ethyloxime | — | 31.7 | EI: m/e = 195 (100%), 167 (21%), 150 (19%), 134 (16%), 125 (20%), 124 (25%), 123 (28%), 106 (16%), 52 (18%), 29 (17%) |
| 8 | 3,4-dihydroxybenzaldehyde O-(4-methyl-benzyl)-oxime | — | 85–86 | APCI-(−): m/e = 256.3 (100%) |
| 9 | 3-ethoxy-4-hydroxy-benzaldoxime | 52005-82-0 | 189 (decomp) | EI: m/e = 181 (90%), 153 (28%), 152 (17%), 136 (26%), 135 (38%), 126 (21%), 110 (100%), 52 (19%), 51 (18%), 29 (16%) |
| 10 | 4-hydroxy-3-methoxy-benzaldoxime | 2874-33-1 | 118.2 | EI: m/e = 167 (100%), 152 (13%), 134 (22%), 125 (21%), 124 (61%), 109 (18%), 106 (19%), 79 (15%), 52 (15%), 51 (16%) |
| 11 | 3,4-dihydroxy-benzaldehyde O-ethyloxime | — | liquid at 23° C. | EI: m/e = 181 (100%), 153 (20%), 152 (19%), 136 (28%), 126 (26%), 110 (47%), 109 (30%), 81 (18%), 53 (14%), 29 (16%) |

Experiment

The tyrosinase inhibition activity of test compounds 1 to 11 was compared with that of kojic acid as follows:

The tyrosinase enzyme extracted from fungi was obtained from Sigma-Aldrich. The tyrosinase (2000 units/mg) was dissolved in phosphate buffer (pH 6.8, 0.067 motl/l) to a concentration of 120 units/ml, and in each case 100 µl of this tyrosinase solution were introduced into a cavity of a microtiter plate made from polystyrene. 25 µl of phosphate buffer (pH 6.8, 0.067 mol/l) and 75 µl of stepwise-diluted test compound 1 to 11 or kojic acid were added. The resulting mixtures were incubated at 37° C. for 10 min. Phosphate buffer (pH 6.8, 0.067 mol/l) was used to dilute the test compounds. The control used was phosphate buffer (pH 6.8, 0.067 mol/l).

100 µl of a 0.03% strength solution of the substrate L-DOPA in phosphate buffer (pH 6.8, 0.067 mol/l) were added, and the absorption (A) was measured at 475 nm using a photometer following incubation for 3 min at 37° C. The residual tyrosinase activities in the presence of Examples 1 to 11 or of kojic acid were calculated in accordance with the following equation:

Residual tyrosinase activity (%)=($A_{Test\ compound}$/$A_{control}$)×100

From the residual tyrosinase activities (%) in a series of dilutions of test compounds, the $IC_{50}$ was calculated for each test compound. This is the concentration of a test compound in which the tyrosinase is 50% inhibited.

TABLE 2

|  | $IC_{50}$ (µM) |
| --- | --- |
| Kojic acid | 22 |
| Test compound 1 | 25 |
| Test compound 2 | 20 |
| Test compound 3 | 18 |
| Test compound 4 | 14 |
| Test compound 5 | 18 |
| Test compound 6 | 4.6 |
| Test compound 7 | 4.2 |
| Test compound 8 | 3 |
| Test compound 9 | 3.5 |
| Test compound 10 | 2.3 |
| Test compound 11 | 0.3 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Skin lightening compositions comprising benzaldoximes selected from the group consisting of:
   4-hydroxybenzaldoxime;
   3,4,5-trihydroxybenzaldoxime;
   3-hydroxy4-methoxybenzaldehyde O-ethyloxime;
   3-ethoxy-4-hydroxybenzaldehyde O-ethyloxime;
   3,4-dihydroxybenzaldoxime;
   3-hydroxy-4-methoxybenzaldoxime;
   4-hydroxy-3-methoxybenzaldehyde O-ethyloxime;
   3,4-dihydroxybenzaldehyde O-(4-methylbenzyl)oxime;
   3-ethoxy-4-hydroxybenzaldoxime;
   4-hydroxy-3-methoxybenzaldoxime; and
   3,4-dihydroxybenzaldehyde O-ethyloxime.

2. Skin lightening compositions according to claim 1 comprising from 0.01% by weight to 30% by weight based on the total weight of the formulation, of said benzaldoximes.

3. Skin lightening compositions according to claim 2 comprising from 0.01% by weight to 20% by weight based on the total weight of the formulation, of said benzaldoximes.

4. Skin lightening compositions according to claim 2 comprising from 0.01% by weight to 5% by weight based on the total weight of the formulation, of said benzaldoximes.

5. A sunscreen composition comprising benzaldoximes selected from the group consisting of:
   4-hydroxybenzaldoxime;
   3,4,5-trihydroxybenzaldoxime;
   3-hydroxy-4-methoxybenzaldehyde O-ethyloxime;
   3-ethoxy-4-hydroxybenzaldehyde O-ethyloxime;
   3,4-dihydroxybenzaldoxime;
   3-hydroxy-4-methoxybenzaldoxime;
   4-hydroxy-3-methoxybenzaldehyde O-ethyloxime;
   3,4-dihydroxybenzaldehyde O-(4-methylbenzyl)oxime;
   3-ethoxy-4-hydroxybenzaldoxime;
   4-hydroxy-3-methoxybenzaldoxime; and
   3,4-dihydroxybenzaldehyde O-ethyloxime.

6. Skin lightening compositions according to claim 1 comprising UVA, UVB filter substances or mixtures thereof.

7. Sunscreen compositions according to claim 5 wherein said composition comprise UVA, UVB filter substances or mixtures thereof.

* * * * *